United States Patent [19]

Azpiri

[11] 4,430,087
[45] Feb. 7, 1984

[54] DISPOSABLE DIAPER

[76] Inventor: Rachel Azpiri, 11925 SW. 43rd St., Miami, Fla. 33175

[21] Appl. No.: 346,307

[22] Filed: Feb. 5, 1982

[51] Int. Cl.³ .............................................. A41F 13/02
[52] U.S. Cl. .................................................. 604/385
[58] Field of Search ....................................... 604/385

[56] References Cited

U.S. PATENT DOCUMENTS

| 3,024,788 | 3/1962 | Lane ..................................... 604/385 |
| 3,274,999 | 9/1966 | Robinson ............................. 604/385 |
| 3,369,545 | 2/1968 | Wanberg .............................. 604/385 |
| 3,585,999 | 6/1971 | Wanberg .............................. 604/385 |
| 3,731,689 | 5/1973 | Schaar .................................. 604/385 |

Primary Examiner—C. Fred Rosenbaum
Assistant Examiner—Sherri Vinyard
Attorney, Agent, or Firm—Millen & White

[57] ABSTRACT

A disposable diaper which includes an absorbent pad, a liquid impervious backing sheet and a plastic storage bag, adapted to store the diaper after use, the bag being attached to an open end of the diaper and stored prior to use in the diaper in a folded condition between the pad and the backing sheet.

9 Claims, 6 Drawing Figures

DISPOSABLE DIAPER

BACKGROUND OF THE INVENTION

This invention relates to disposable diapers.

Disposable diapers usually include an absorbent sheet, a liquid impervious backing sheet, and frequently, a layer of absorbent batting therebetween. Being readily disposable and adapted for one time use, the need for laundering is eliminated. However, the soiled diapers present difficulties because they tend to generate undesirable odors when stored prior to disposal. Disposable diapers in the prior art have been provided with disposable covers attached to, or integral with the backing sheet of the diaper. Examples of such prior art disposable diapers are disclosed in U.S. Pat. Nos. 3,604,423; 3,865,110; 3,877,432; 3,920,019. Such prior art disposable diapers suffer from the disadvantages that the covers are exposed, which renders the diapers difficult or cumbersome to apply to the body and the covers susceptible to soiling. U.S. Pat. No. 3,274,999 discloses an anatomical dressing provided with an envelope element adapted to be folded and stored in a central portion of the dressing. Although this renders the dressing easy to use when the envelope is in a stored condition, the envelope is difficult to remove from the dressing without disturbing the dressing per se.

OBJECTS OF THE INVENTION

It is an object of the present invention to provide a disposable absorbent diaper with an attached storage bag that is stored, in a compact condition, within the diaper prior to and during use of the diaper.

It is a further object of the invention to provide a disposable absorbent diaper with a storage bag which can be retrieved from a concealed location in the diaper with a minimum of disturbance to the diaper.

Yet a further object of the invention is to provide a disposable diaper with a storage bag that is stored in the interior of the diaper in such fashion that it can be retrieved from the interior of the diaper with a minimum of disturbance to the diaper, with a portion of the storage bag attached to the diaper when the storage bag is retrieved from the interior of the diaper.

SUMMARY OF THE INVENTION

The disposable diaper of the present invention comprises an absorbent compressible pad positioned between an absorbent sheet and a liquid impervious backing sheet, and a storage absorbent sheet bag, for storing the pad and backing sheet therein after use, attached to one end of the diaper and stored in a folded condition inside the diaper prior to and during use thereof.

More specifically, this invention relates to a disposable diaper having a foldable generally rectangular pad of absorbent material positioned between an absorbent sheet and a flexible liquid-impervious backing sheet and a tubular storage bag formed of flexible, liquid-impervious sheet material, which is open at one end and closed at the other, affixed to one end of the diaper and dimensioned to receive the diaper after use when folded to the dimensions of the bag, wherein one end of the diaper is openable to expose the interior of the diaper, the bag is stored proximate the open end of and within the interior of the diaper and the open end of the diaper comprises means to retain the bag within the interior of the diaper prior to and during use of the diaper.

DETAILED DESCRIPTION OF THE INVENTION

Figure 1:
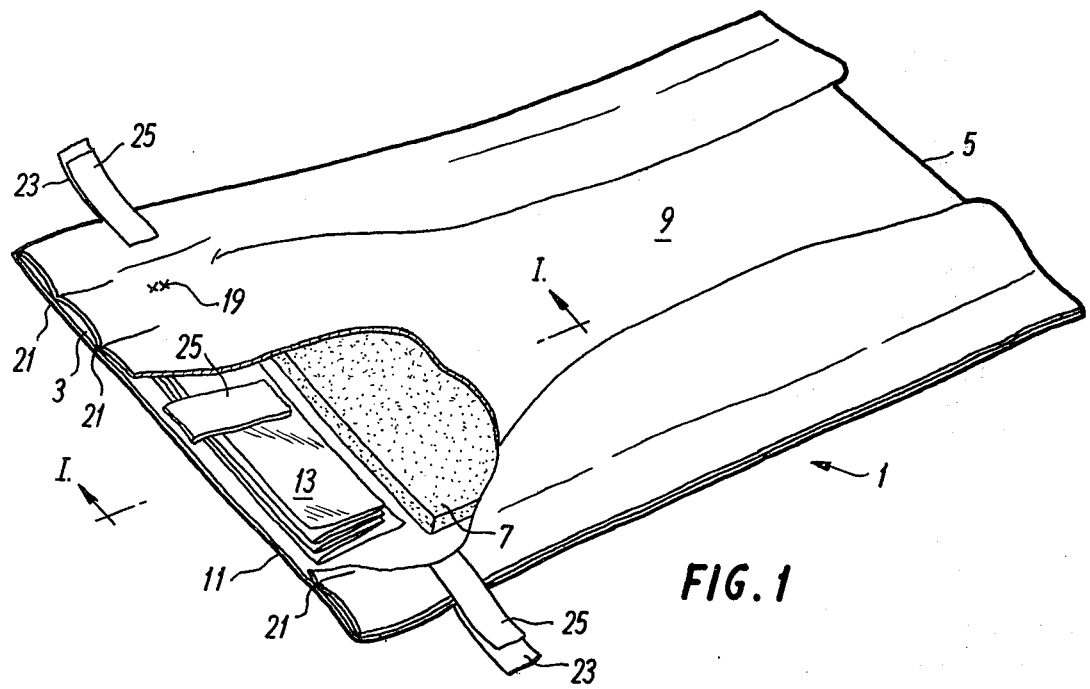
FIG. 1 is a perspective view of a preferred embodiment of the invention prior to use, with a portion broken away showing the storage bag stored in a folded condition in the diaper.
Figure 2:
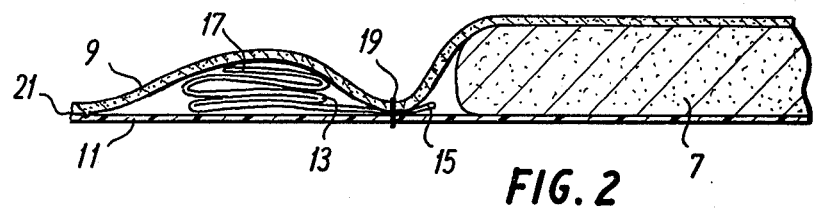
FIG. 2 is a fragmentary longitudinal cross-sectional view of FIG. 1 taken generally along line I—I of FIG. 1.

Referring now to FIGS. 1 and 2, there is shown a disposable diaper designated generally as 1, having an openable end 3 and a closed second end 5. The diaper comprises an absorbent pad 7 positioned between an absorbent sheet 9 and a liquid impervious backing sheet 11. Sheet 9 thus constitutes the absorbent face of the diaper and sheet 11 comprises the liquid impervious face of the diaper. A generally tubular storage bag 13 having a closed end 15 and open end 17 is stored in a folded condition between the liquid impervious backing sheet 11 and the absorbent sheet 9 and is suitably bonded thereto at intervals 19 proximate the open end 11 of the diaper 1. The absorbent sheet 9 and backing sheet 11 are spot bonded together at intervals 21 along the otherwise open end 11 of diaper 1, which serves to removably retain the bag 13 in its stored, folded condition between the absorbent sheet 9 and the liquid impervious backing sheet 11. The absorbent sheet 9 and the liquid impervious backing sheet 11 are bonded together at intervals 21 by an adhesive or by heat sealing. Adhesive tabs 23 with removable sheets 25 covering the adhesive bearing faces of tabs 23 are provided to secure the sides of closed end 5 to the sides of open end 3 of the diaper when the diaper has been placed around the crotch of the infant and the open end 3 at least partially encircles the infant's waist. Adhesive tab 25 with a removable cover sheet 27 is attached to the open end 17 of bag 13 to seal bag 13 when the soiled diaper is stored therein.

Figure 4:
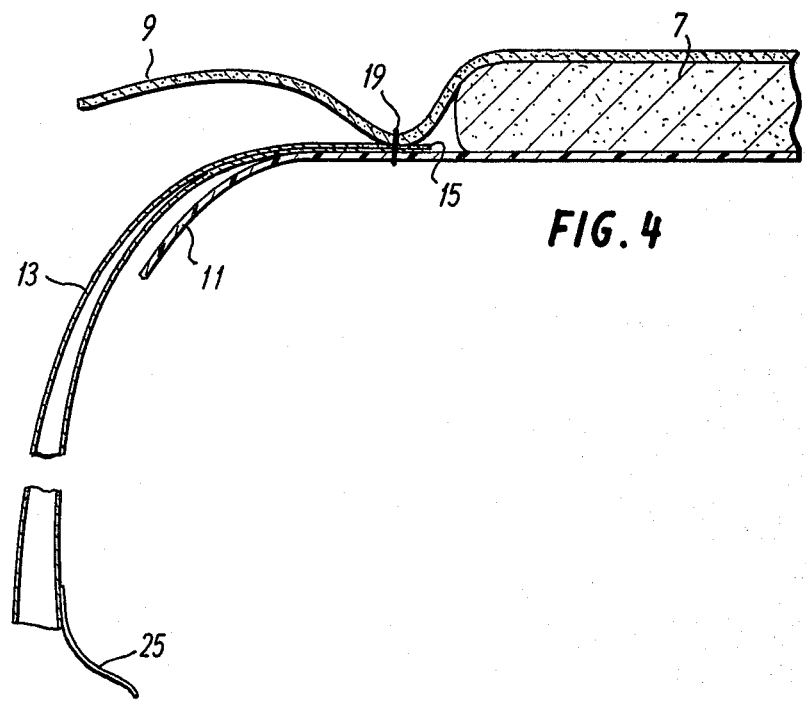
FIG. 4 is a fragmentary longitudinal cross-sectional view of FIG. 3, taken generally along line III—III of FIG. 3.
Figure 3:
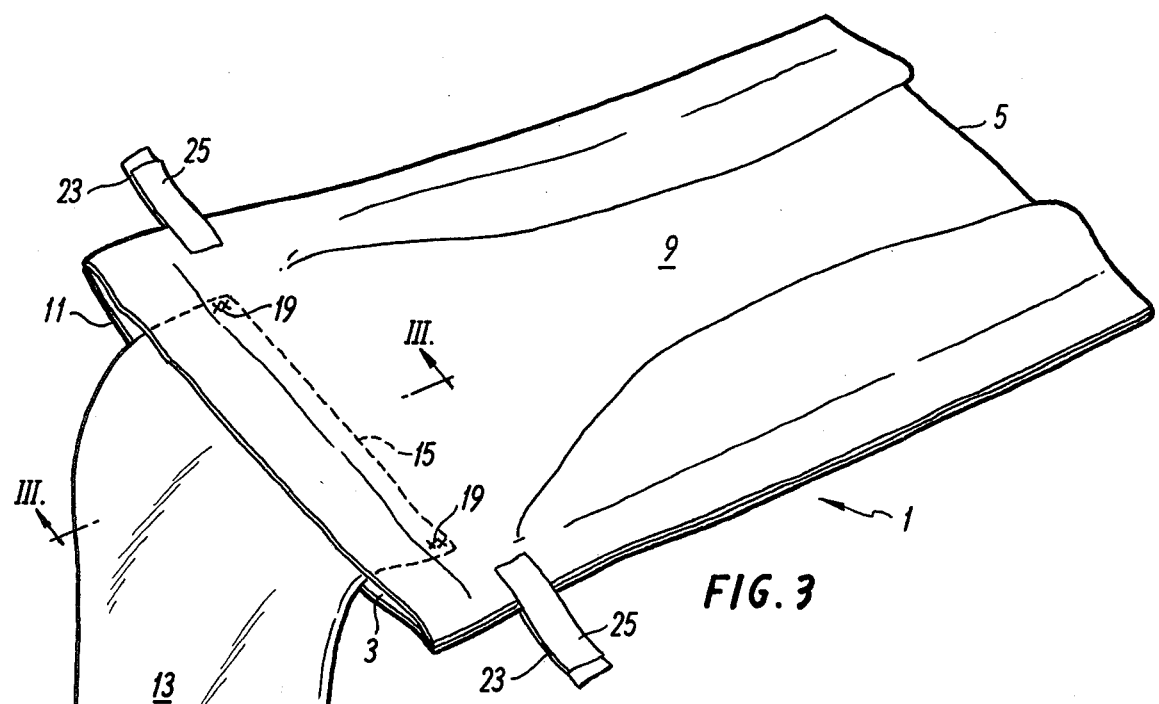
FIG. 3 is a perspective view of the preferred embodiment of FIG. 1 after use, showing the storage bag deployed for storage of the used diaper.

Referring now to FIGS. 3 and 4, the diaper 1 is shown with storage bag 13 deployed. Bag 13 is suitably attached at points 19 within the open end 3 of the diaper at the corners of its closed end 15.

Figure 5:
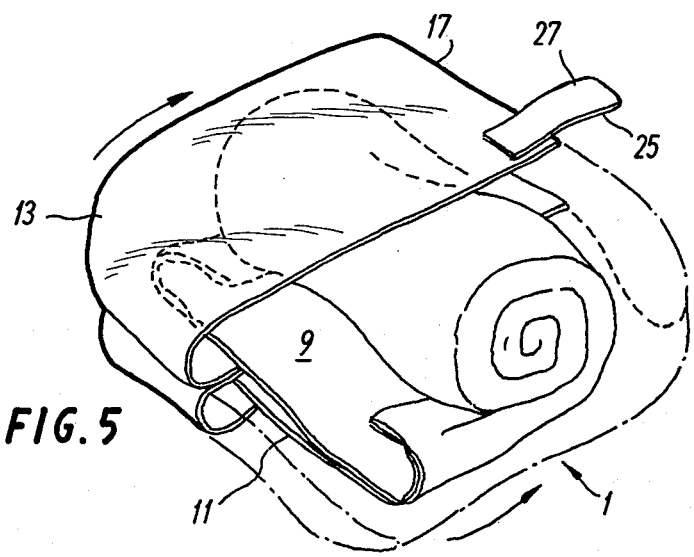
FIG. 5 is a perspective view of the preferred embodiment of FIG. 1 after use, showing the storage bag, with a portion thereof broken away, everted and covering the folded diaper.

Referring to FIG. 5, the used diaper 1 is shown in rolled condition with bag 13, shown with a portion broken away, everted to enclose diaper 1. Adhesive tab 25 maintains open end 17 of bag 13 in a closed position after diaper 1 is stored therein.

Figure 6:
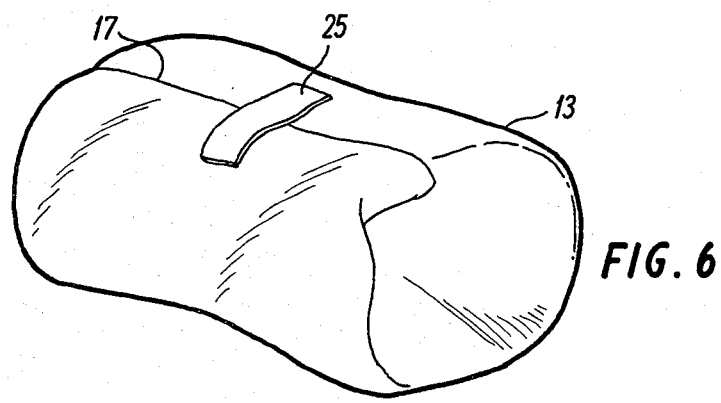
FIG. 6 is a perspective view of the preferred embodiment of FIG. 1 after use, showing the everted storage bag completely enclosing the diaper and sealed for disposal.

Referring to FIG. 6, bag 13 is shown completely encasing diaper 1 with adhesive tab 25 maintaining bag 13 in a closed condition.

In use, diaper 1 is placed around the crotch of the infant and adhesive tabs 23 with sheets 25 removed therefrom are used to secure the ends 3 and 5 of the diaper to each other as they encircle the waist of the infant. When the diaper has become soiled, access to bag 13 is gained by separating the backing sheet 3 from the absorbent sheet 9 by breaking bonding spots at intervals 21. Bag 13 is then deployed as shown in FIG. 3 by manually unfolding from the interior of the diaper. Diaper 1 is then rolled transverse to the longitudinal axis of the diaper from closed end 5 to open end 3.

Bag 13 is then everted over the rolled diaper 1 until bag 13 completely covers the rolled diaper. The open end 17 of bag 13 is then folded over and the adhesive strip 25 is then used, after removal of protective sheet 27, to maintain bag 13 in closed condition.

What is claimed is:

1. In a disposable diaper having a folded generally rectangular pad of absorbent material positioned between an absorbent sheet and a flexible liquid-impervious backing sheet and a tubular storage bag formed of flexible, liquid-impervious sheet material, which is open at one end and closed at the other, affixed to one end of the diaper and dimensioned to receive the diaper after use when folded to the dimensions of the bag, the improvement wherein one end of the diaper is openable to expose the interior of the diaper, the bag is stored proximate the open end of and within the interior of the diaper, the bag is secured at its closed end to the interior of and proximate the open end of the diaper, and the open end of the diaper comprises means to retain the bag within the interior of the diaper prior to and during use of the diaper.

2. The disposable diaper of claim 1, wherein the bag is stored prior to use between the pad and the backing sheet and the backing sheet is removably secured to the pad at intervals along the open end of the diaper to removably retain the bag within the diaper.

3. The disposable diaper of claim 2, wherein the backing sheet is spot bonded to the pad at intervals along the open end of the diaper to removably retain the bag prior to use within the diaper.

4. The disposable diaper of claim 1, wherein the bag is secured at its closed end to at least one of the backing sheet and the pad.

5. The disposable diaper of claim 4, wherein the closed end of the bag is spot bonded to both the pad and the backing sheet at at least one corner of the closed end of the bag.

6. The disposable diaper of claim 1 comprising means to maintain the bag in closed condition after the diaper is stored therein.

7. The disposable diaper of claim 1, wherein the bag is stored prior to use between the pad and the backing sheet, the backing sheet is spot bonded to the pad at intervals along the open end of the diaper to removably retain the bag prior to use within the diaper, and the bag is spot bonded at at least one corner of its closed end to at least one of the pad and the backing sheet.

8. The disposable diaper of claim 7, wherein the bag is spot bonded to both the pad and the backing sheet at at least one corner of the closed end of the bag.

9. The disposable diaper of claim 8 comprising means for maintaining the open end of the bag in a closed position after the diaper is stored therein.

* * * * *